(12) United States Patent
Khouri

(10) Patent No.: US 8,905,924 B2
(45) Date of Patent: Dec. 9, 2014

(54) ILLUMINATED DENTAL PROP

(76) Inventor: Louie Khouri, New York, NY (US)

( * ) Notice: Subject to any disclaimer, the term of this patent is extended or adjusted under 35 U.S.C. 154(b) by 1371 days.

(21) Appl. No.: 11/877,982

(22) Filed: Oct. 24, 2007

(65) Prior Publication Data

US 2008/0096155 A1 Apr. 24, 2008

Related U.S. Application Data

(60) Provisional application No. 60/862,660, filed on Oct. 24, 2006.

(51) Int. Cl.
*A61B 1/32* (2006.01)
*A61C 3/00* (2006.01)
*A61C 1/08* (2006.01)
*A61C 5/14* (2006.01)

(52) U.S. Cl.
CPC .. *A61C 1/088* (2013.01); *A61C 5/14* (2013.01)
USPC .............................................. 600/238; 433/29

(58) Field of Classification Search
USPC ........................ 600/238; 433/140, 29; 257/81
See application file for complete search history.

(56) References Cited

U.S. PATENT DOCUMENTS

| 4,752,428 | A | * | 6/1988 | Williams et al. ................. 264/83 |
| 5,959,433 | A | | 9/1999 | Rohde |
| 6,119,864 | A | * | 9/2000 | Kessler et al. ................. 206/704 |
| 6,190,018 | B1 | * | 2/2001 | Parsons et al. ................. 362/116 |
| 6,332,776 | B1 | | 12/2001 | Martin et al. |
| 6,830,451 | B1 | | 12/2004 | Bayat |
| 2004/0063060 | A1 | | 4/2004 | Meyers et al. |
| 2005/0239017 | A1 | | 10/2005 | Lim |
| 2005/0239018 | A1 | | 10/2005 | Green et al. |
| 2006/0176685 | A1 | * | 8/2006 | Galli et al. ..................... 362/157 |

* cited by examiner

*Primary Examiner* — Christian Sevilla
(74) *Attorney, Agent, or Firm* — Harness, Dickey & Pierce, PLC

(57) ABSTRACT

The present invention relates to an illuminated dental prop for holding a patient's mouth open during dental procedures. The illuminated dental prop is completely disposed within the patient's mouth during use and includes a body portion and a lighting assembly that is selectively detachable from the body to allow for intense sterilization of the components after use. Under certain embodiments of the invention, the body portion and/or the lighting assembly will be disposable after a single use.

11 Claims, 4 Drawing Sheets

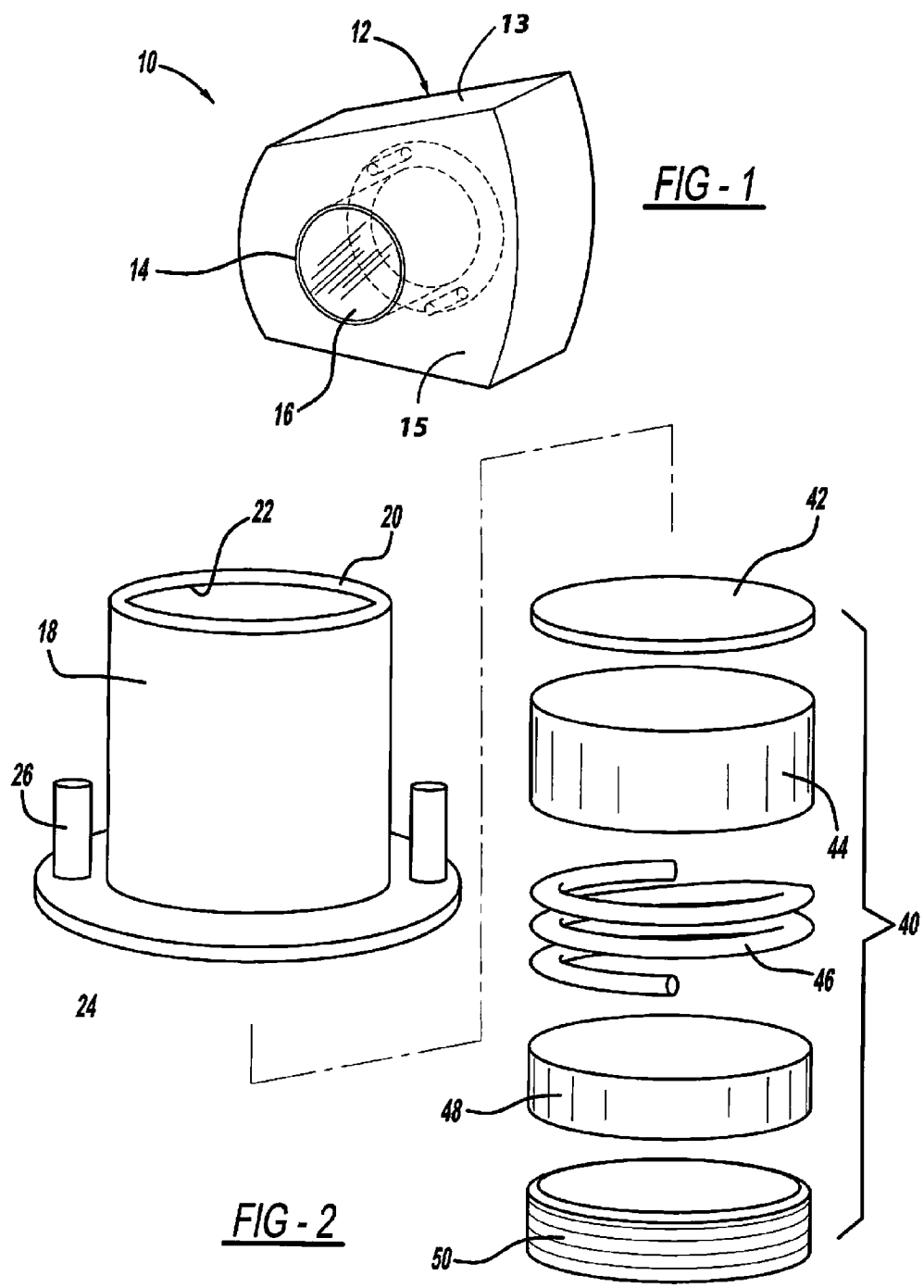

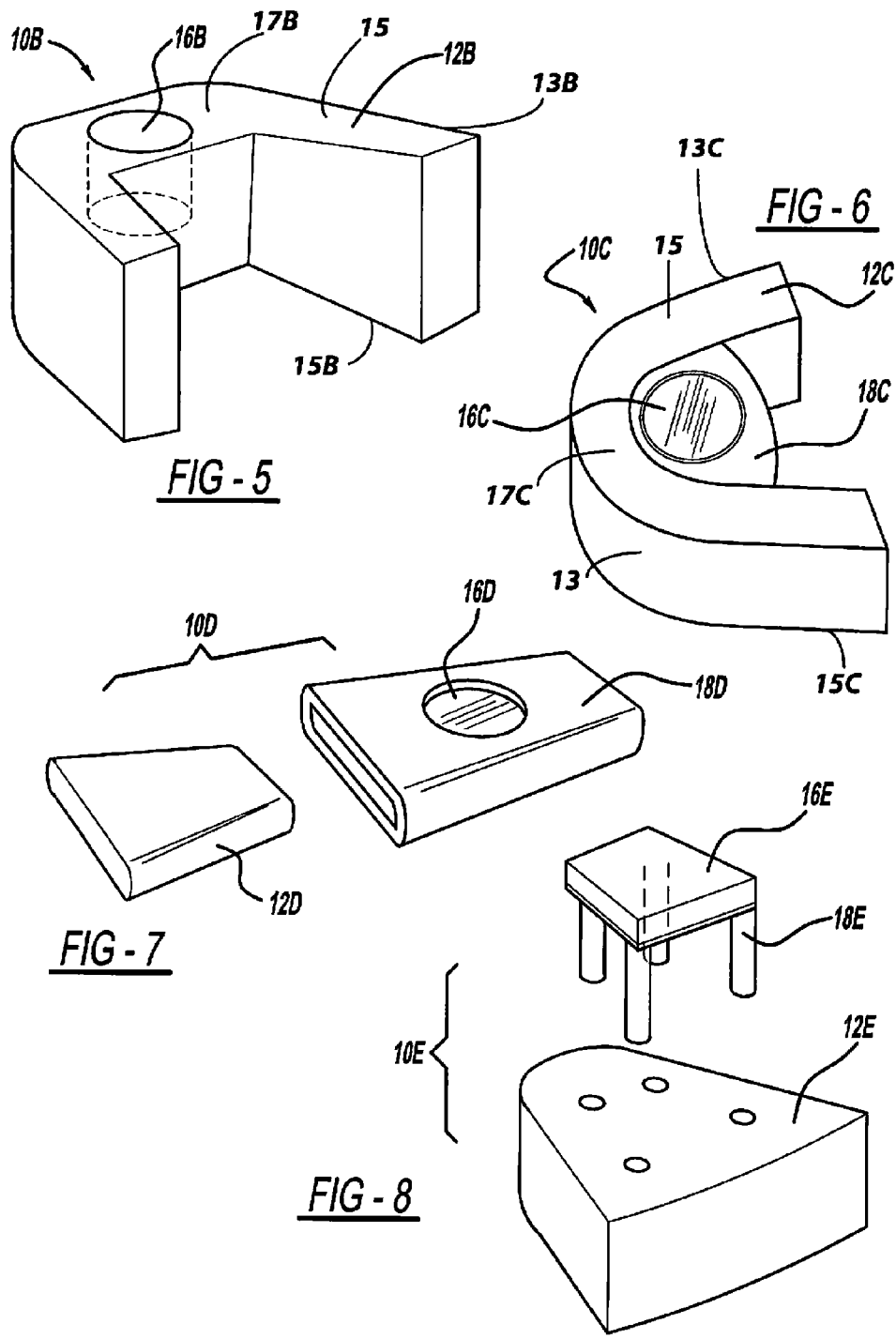

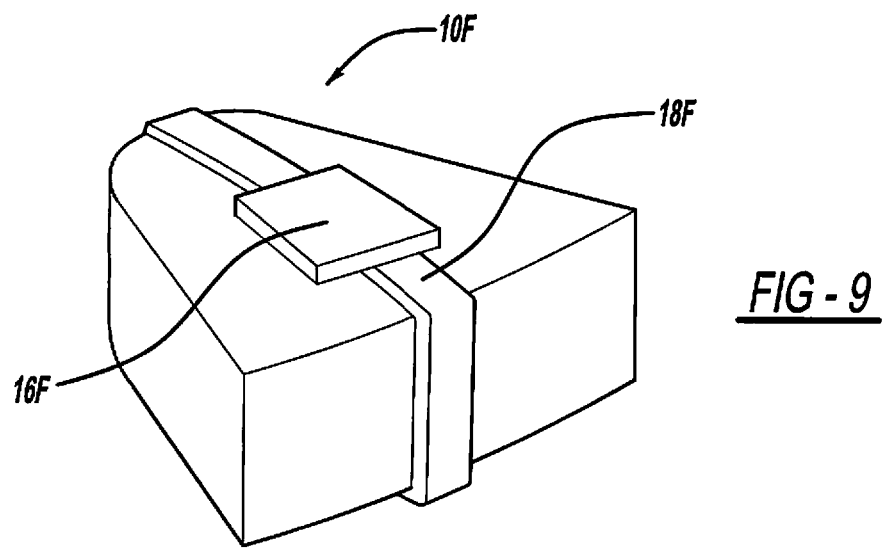

ILLUMINATED DENTAL PROP

CROSS-REFERENCE TO RELATED APPLICATIONS

This application claims the benefit of U.S. Provisional Application No. 60/862,660, filed on Oct. 24, 2006. The disclosure of the above application is incorporated herein by reference.

BACKGROUND

1. Field of the Invention

The present invention generally relates to illuminated dental props for holding the mouth open during dental procedures. Dental props, per se, are known to come in a variety of shapes and sizes such as wedge-shaped props and C-shaped props by way of non-limiting example. Generally the props are placed between the upper and lower teeth, opposite the side of the mouth which needs to be accessed by a dental practitioner. However, with regard to accessing and viewing the target area by the dental practitioner, currently available dental props do nothing to enhance the visibility within the oral cavity to carryout the necessary procedure.

Further, while various light sources are available to assist in illuminating the oral cavity, such devices are positioned outside of the oral cavity with the light source directed at the target area. However, external light sources tend to be somewhat ineffective. Thus, the present invention relates to the incorporation of a light assembly with a dental prop of desired size and shape.

2. Description of the Prior Art

Relatively recently a handful of patents and patent applications directed to the general concept of combining a light source with a dental prop have surfaced. One such patent is U.S. Pat. No. 6,332,776 which issued Dec. 6, 2001 to Martin et al. According to one embodiment disclosed, a unitary body formed to include a first cavity having an inclined reflective surface is disclosed. Light projecting from a light source connected to a light conducting cable is projected upon the reflective surface to emit light within the patient's mouth. Under a second embodiment, a dental prop is constructed including a cavity which hosts the lighting elements including a primary induction coil connected to a secondary induction coil. Under all embodiments disclosed, there does not appear to be any teaching or disclosure of a light assembly which is conveniently detachable from the body of the dental prop.

Alternatively, US Patent Publication No. US/2005/0239018 discloses a lighted dental prop wherein the light source is integrated in a permanently fixed relationship with the body of the bite block. Under this scenario, either the entire construction would be discarded after a single use or the product as a whole is sterilized for reuse. There does not appear to be any disclosure as to replacement of the light source if need be which is another apparent design flaw.

A perceived problem with each of the above-referenced teachings is that the light source is not readily removable from the bite block such that the bite block portion can be sterilized or discarded after a single use. Further, the light assembly is either integral with the bite block portion or requires extreme work to detach the same from the bite block.

SUMMARY

The present invention provides for an illuminated dental prop for holding the dental patient's mouth open during dental procedures which incorporates a selectively removable light source. In addition to providing much needed light to the oral cavity of a patient, a significant advantage over the above noted references is the ability to readily remove the light assembly from the bite block to facilitate sterilization of the light assembly and, under certain embodiments, discarding of the bite block portion. The dental props of the present invention are designed to be of a size and geometry to be fully contained within the patient's mouth, i.e., without wires extending out of the mouth, to ensure clearance in the oral cavity of the patient such that the practitioner can access the target area with the necessary dental instruments.

DRAWINGS

The drawings described herein are for illustration purposes only and are not intended to limit the scope of the present disclosure in any way.

FIG. 1 is a perspective view of a first embodiment of the illuminated dental prop assembly;

FIG. 2 is a blown apart perspective view of the illuminated dental prop of FIG. 1;

FIG. 5 is a perspective view of an alternate illuminated dental prop;

FIG. 6 is a perspective view of an alternative illuminated dental prop wherein the light assembly is retro-fit to an existing convention dental prop;

FIG. 7 is an alternative illuminated dental prop assembly including a lighted sleeve disposable over the body of a dental prop;

FIG. 8 is an alternative illuminated dental prop assembly including a lighted pliable attachment disposable over the body of a dental prop; and FIG. 9 is an alternative illuminated dental prop assembly including a lighted band disposable over the body of a dental prop.

DETAILED DESCRIPTION

Figure 3:
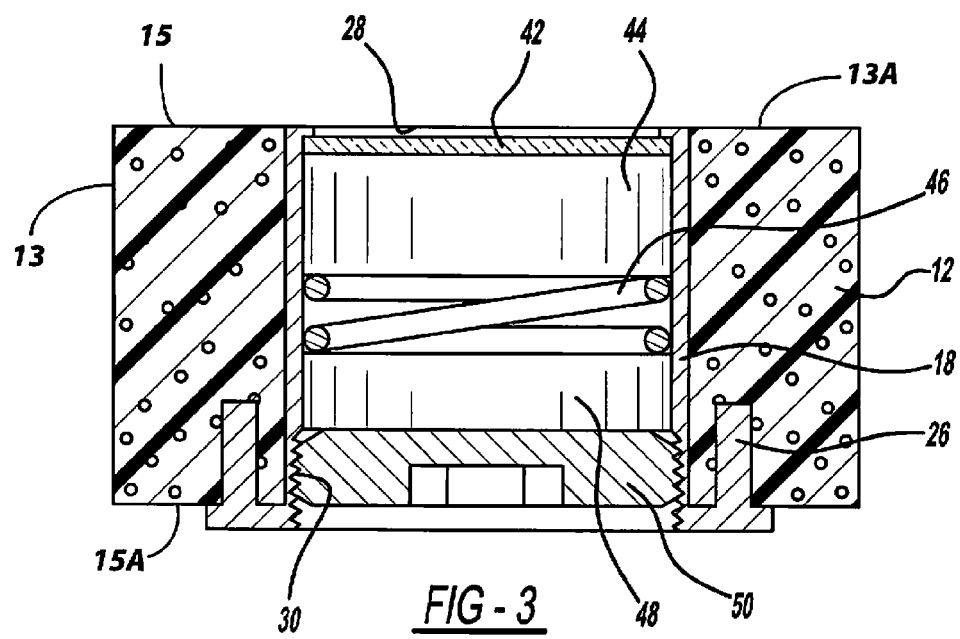
FIG. 3 is a sectional view of the illuminated dental prop assembly of FIGS. 1 and 2.

The following description is merely exemplary in nature and is not intended to limit the present disclosure, application, or uses. It should be understood that throughout the drawings, corresponding reference numerals indicate like or corresponding parts and features.

The first illuminated dental prop in accordance with the teachings of the present invention is shown with reference to FIGS. 1-3. Initially, referring to FIG. 1, there is shown the illuminated dental prop 10 which includes a body 12 which forms the bite block portion of the assembly and a light assembly 16 which is mounted through an aperture 14 of the body 12. The body 12 can be in many shapes or configurations and is shown according to the first embodiment as a wedge-shaped bite block having upper and lower teeth engaging surfaces 13 and 13A and first and second substantially perpendicular sidewalls 15 and 15A. The light assembly 16 which is selectively detachable from the body of the bite block generally includes a housing 18 and a light source 40. The housing 18 includes a sleeve 20 including a longitudinally central bore 22 for hosting the light source 40. The sleeve 20 includes in inwardly extending lip 28 at one end and a threaded interior lead-in portion 30 along the opposite end of lip 28. The housing 18 also includes an integral outwardly extending flange disposed along the end opposite lip 28 which may optionally include one or more posts 26 which seat into the body 12 of the bite block to assist in securing the lighting assembly.

The light source 40 according to the first embodiment 10 generally includes a lens 42 disposed against the inwardly extending lip 28 of the housing 18, a lighting element 44, an electrical contact 46, a battery 48, and a threaded end cap 50. As should be understood by those skilled in the art, as the threaded end cap 50 is rotated to an extent such that the battery is in sufficient electrical contact with the lighting element through electrical contact 46, the lighting element 44 becomes illuminated and remains illuminated until such time that the threaded end cap is sufficiently backed away. According to this embodiment, the lighting element 44 is in the form of a miniature light bulb; however, as will be described in further detail below, alternative lighting means may be utilized.

Figure 4:
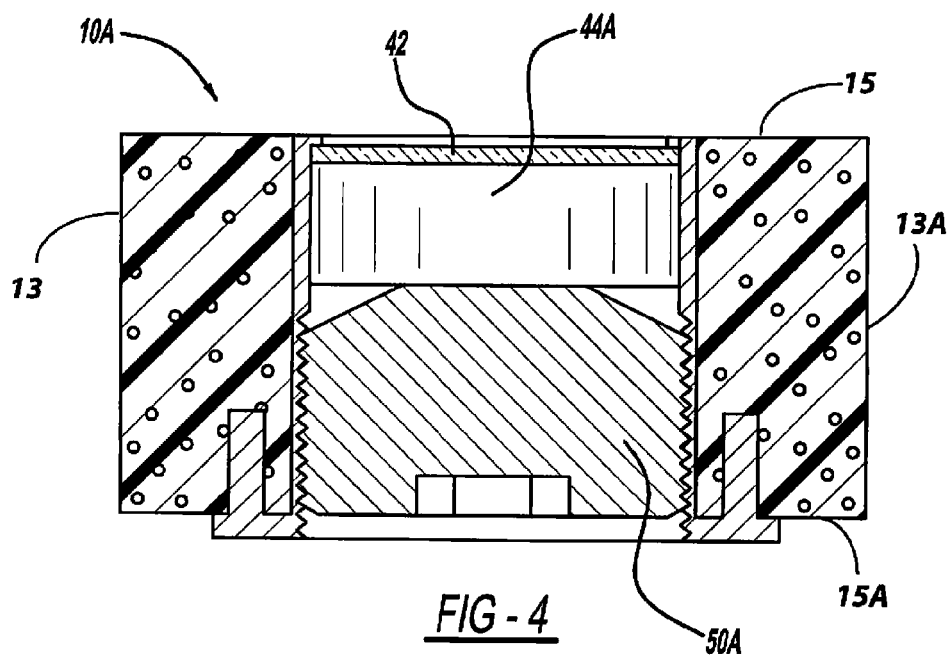
FIG. 4 is a sectional view of an alternative illuminated dental prop featuring a different lighting assembly.

Referring to FIG. 4, there is shown a first alternative illuminated dental prop embodiment 10A wherein the lighting element 44A is activated by the threaded end cap 50A which is in the form of an induction element. As should be understood by those skilled in the art, the induction element 50A is activated by another induction coil (not shown) via electromagnetic energy.

In addition to the dental props shown in FIGS. 1-3 and 4, respectively, it should be understood that the lighting assembly may be employed with those or other dental prop bodies. For example, the lighting assembly may be an LED light package including an LED light source and a battery. This assembly may be two separate components or may be in the form of a self-contained assembly which is attached to the dental prop body. Whatever light assembly is employed, it is envisioned the light assembly will have a useful life which affords the end user the option of reusing the light assembly after appropriate sterilization by inserting it into a fresh dental prop body. Thus, a kit having at least one selectably reusable light assembly along with a plurality of disposable dental props may be provided commercially.

Alternately, a reusable dental prop with a plurality of detachable, disposable light assemblies is also envisioned.

Regardless of the dental prop body design, generally the upper and lower teeth will sit in a stable position on the respective upper and lower teeth engaging surface.

Referring to FIG. 5, there is yet another alternative embodiment 10B which includes a lighting assembly 16B disposed within an operative along a central portion of the body 12B of the bite block assembly. As can be seen from FIG. 5, the body is substantially C-shaped such that the bite block provides sufficient clearance so that it does not interfere with the dental practitioner during a dental procedure. Thus, the C-shaped body is defined by first and second forward projecting portions which are engaged by the teeth 13 and 13B (teeth engaging surfaces), a central body portion 17B which is positioned toward the back of the mouth and sidewalls 15 and 15B.

Referring to FIG. 6, yet another alternative embodiment 10C is depicted. The body 12C also generally has a C-shaped body and the lighting assembly 16C, rather than being embedded within the body, is in the form of a selectively detachable unit which is mounted within the concave recess along the interior wall of the body 12C. The body includes teeth engaging surfaces 13 and 13C, a central body portion 17C and first and second sidewalls 15 and 15C on opposite sides of the body. This embodiment is considered to be an option for retro-fitting currently commercially available bite blocks. The lighting assembly 16C may be mechanically attached via a male and female coupling with the body or adhesively attached within the recess.

Referring to the embodiment of FIG. 7 referenced by the numeral 10D, the bite block body 12D fits within a pliable sheath. The sheath serves as the housing 18D and hosts the lighting assembly 16D.

Referring to FIG. 8, another embodiment 10E is depicted wherein the body 12E includes a plurality of openings for receiving the platform-type housing 18E having mounted thereto a light assembly 16E.

Referring to FIG. 9, another embodiment 10F is shown as including a housing 18F in the form of a band having attached thereto a light assembly 16F. The band can be formed from various materials including elastic by way of non-limiting example. This type of structure would be ideal for retro-fitting commercially available bite blocks including wedges as well as C-shaped bite blocks with lighting to illuminate the oral cavity.

The illuminated dental props of FIGS. 6-9, preferably employ a self contained LED light as the light source. As should be understood by those skilled in the art, the LED lighting should illuminate the oral cavity to an appreciably extent but, should not generate light that falls within the light range that would promote undesired curing of any materials employed in the dental procedure being carried out. Additionally, the lighting assembly shall not generate as unacceptable level of heat which could be uncomfortable to a patient.

The body 12C which is generally formed from a moldable thermoplastic or elastomeric material may include a slot (not shown) along the concave recess into which the lighting assembly 16C is press fit. The slot may include a locking mechanism such that when the lighting assembly is disposed therein the battery will be activated.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An illuminated dental prop for insertable into a patient's mouth for lighting an oral cavity, comprising:
    a body including a first distal end, a second distal end, first and second sidewalls, and first and second teeth engaging surfaces extending between and interconnecting said first and second distal ends, said first and second teeth engaging surfaces being angled relative to each other such that a first distance between said first and second teeth engaging surfaces proximate said first distal end is less than a second distance between said first and second teeth engaging surfaces proximate said second distal end, said body being adapted to be received between upper and lower teeth in the patient's mouth and maintain the patient's mouth in an open position such that the entire dental prop is contained within the patient's mouth; and
    a lighting assembly attached to said body during use and including a light source and a battery for activating the light source, said light source being disposed between said first and second distal ends and between said first and second teeth engaging surfaces in a direction of said first sidewall which is capable of facing the patient's oral cavity to thereby project light into the oral cavity, said lighting assembly being selectively detachable from said body without disassembling said body.

2. The illuminated dental prop of claim 1 wherein at least one of said body and said light source are disposable after a single use.

3. The illuminated dental prop of claim 1 wherein said light source is an LED assembly.

4. The illuminated dental prop of claim 1 wherein said lighting assembly is mechanically fastened to said body via a male and female connector, whereby upon making the connection, the battery is engaged by the light source thereby activating the lighting assembly.

5. The illuminated dental prop of claim 1 wherein said body is formed from a material selected from the group consisting of thermoplastic, thermosets and foams.

6. The illuminated dental prop of claim 1 wherein said body is substantially C-shaped and said first and second teeth engaging surfaces define first and second spaced apart projections extending from a central body portion.

7. The illuminated dental prop of claim 6 further comprising a recess defined by the inner wall of said C-shaped body whereby said lighting assembly is substantially disposed within said recess.

8. The illuminated dental prop of claim 6 wherein said body includes an aperture receiving the light assembly.

9. The illuminated dental prop of claim 8 wherein said aperture occurs along said central body portion connecting the first and second projections.

10. The illuminated dental prop of claim 1, wherein said body and said lighting assembly are fully contained within the patient's mouth during use.

11. The illuminated dental prop of claim 1, wherein said lighting assembly is mechanically fastened to said body via a male and female connector.

* * * * *